(12) United States Patent
McBride-Sakal et al.

(10) Patent No.: US 6,471,987 B1
(45) Date of Patent: Oct. 29, 2002

(54) DRUG RELEASING ELASTIC BAND AND METHOD

(75) Inventors: Marcia McBride-Sakal; Michael S. Banik, both of Bolton; Kathleen M. Miller, Shrewsbury, all of MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/328,665

(22) Filed: Jun. 9, 1999

(51) Int. Cl.[7] .......................... A61K 9/70; A61K 47/00; A61B 17/12
(52) U.S. Cl. ................ 424/447; 424/422; 424/423; 424/424; 424/426; 424/443; 424/444; 424/484; 424/485; 424/486; 514/772; 514/772.3; 514/782; 514/953; 606/151; 606/157
(58) Field of Search ................. 424/446–449, 424/422, 423, 424, 426, 443, 444, 447, 484, 485, 486; 514/772, 772.3, 782, 953; 606/151, 157

(56) References Cited

U.S. PATENT DOCUMENTS

| | | | | |
|---|---|---|---|---|
| 4,289,749 A | * | 9/1981 | Keith et al. | 514/653 |
| 4,483,341 A | * | 11/1984 | Witteles | 606/21 |
| 5,224,497 A | * | 7/1993 | Ehlers | 128/898 |
| 5,310,559 A | * | 5/1994 | Shah et al. | 424/448 |
| 5,403,595 A | * | 4/1995 | Kitchell et al. | 424/501 |
| 5,443,458 A | | 8/1995 | Eury | 604/891.1 |
| 5,462,743 A | * | 10/1995 | Turner et al. | 424/448 |
| 5,618,286 A | | 4/1997 | Brinker | 606/60 |
| 5,976,158 A | * | 11/1999 | Adams et al. | 606/140 |

FOREIGN PATENT DOCUMENTS

| EP | 0 477 020 | 3/1992 |
|---|---|---|
| WO | WO 89/04674 | 6/1989 |

* cited by examiner

Primary Examiner—Jose' G. Dees
Assistant Examiner—Frank Choi
(74) Attorney, Agent, or Firm—Kenyon & Kenyon

(57) ABSTRACT

A ligating band according to the present invention comprises an elastomeric layer and an inner drug releasing layer. The inner drug releasing layer includes a therapeutic agent, for example a chemotherapeutic agent for treating a mucosa, polyp or other growth. A ligating band according to the present invention also may include an inner diffusion barrier disposed between the elastomeric layer and the inner drug releasing layer, with the elastomeric layer and the inner drug releasing layer each contacting the inner diffusion barrier.

23 Claims, 4 Drawing Sheets

DRUG RELEASING ELASTIC BAND AND METHOD

FIELD OF THE INVENTION

The present invention relates to tissue ligation, and in particular a ligating band which releases a drug, for example a chemotherapeutic agent.

BACKGROUND INFORMATION

Endoscopic ligation is often used to treat polyps or other growths inside the body. For example, pre-malignant gastrointestinal mucosa are often removed using an endoscopic snare, and endoscopic ligation may be employed to remove surrounding residual or base tissue, particularly when biopsy of the earlier-removed tissue indicates a foci of cancer. In other cases, mucosa may be removed by delivering a ligating band to the base of the mucosa. The ligating band restricts blood flow to the ligated tissue, leading to eventual necrosis.

One problem with treating pre-malignant or malignant mucosa endoscopically is that the base of the malignancy may not undergo necrosis. If some malignant or pre-malignant cells are left surviving, there is a risk that the residual cancer cells will spread further. For this reason, many physicians opt for surgical treatment of such mucosa. However, surgical resection is not desirable or even possible for some patients, and surgical recision is a much more invasive and complicated procedure, even for more healthy patients.

SUMMARY OF THE INVENTION

A ligating band according to the present invention comprises an elastomeric layer and an inner drug releasing layer. The inner drug releasing layer includes a therapeutic agent, for example a chemotherapeutic agent. A ligating band according to the present invention also may include an inner diffusion barrier disposed between the elastomeric layer and the inner drug releasing layer, with the elastomeric layer and the inner drug releasing layer each contacting the inner diffusion barrier.

DETAILED DESCRIPTION

Figure 1:
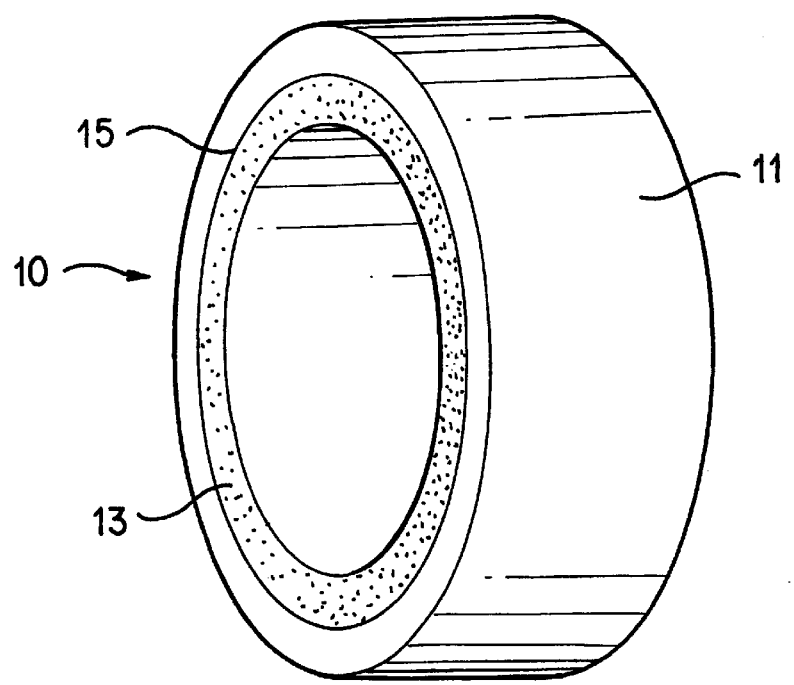
FIG. 1 is a perspective view of an exemplary embodiment of a ligating band according to the present invention.

FIG. 1 illustrates an exemplary embodiment of a ligating band 10 according to the present invention. In general, it is understood that a ligating band according to the present invention may be delivered using any suitable delivery device or mechanism. Such a device may include, for example, a cylindrical end over which one or more ligating bands may be stretched. Tissue to be ligated may be drawn into an interior recess of the cylindrical end, and a band released around the base of the tissue. Such tissue may include pre-malignant or malignant mucosa, other polyps, varices, ulcers, or any other type of tissue. For convenience, any tissues to be ligated are referred to herein as mucosa, but it is understood that this term includes the above types of tissue as well as any other tissue which may be subject to ligation. Likewise, it is understood that the term "ligating band" should be generally construed herein to include any suitable elastic band, and the term "ligation" should be generally construed to include any suitable procedure for delivering such a band.

In the exemplary embodiment of FIG. 1, ligating band 10 includes an elastomeric layer 11 and an inner drug releasing layer 13. Elastomeric layer 11 and inner drug releasing layer 13 may be separated by an inner diffusion barrier 15, so that each contacts inner diffusion barrier 15. Elastomeric layer 11 preferably provides an elastic force to retain ligating band 10 in place around the base of a mucosa. Elastomeric layer 11 is therefore preferably a material having a relatively high elasticity. Elastomeric layer may also be relatively impervious to destruction within the body, so that the elasticity of elastomeric layer 11 does not significantly decrease over time.

Inner drug releasing layer 13 may be impregnated or coated with a therapeutic agent, for example a time-released therapeutic agent, that may treat a ligated mucosa or the surrounding tissue. While any material may be used, inner drug releasing layer 13 preferably is formed from a biodegradable material, for example a biodegradable polymer, that breaks down over time. Many biodegradable materials are readily impregnated or coated with therapeutic agents, and the processing parameters for loading drugs into biodegradable materials are well established for many such materials. In addition, use of a biodegradable material for inner drug releasing layer 13 allows for lower processing temperatures during manufacture. The lower processing temperature helps prevent drug degradation and expands the arsenal of therapeutics that may be used in conjunction with a ligating band 10 according to the present invention. Preferred materials include polylactic acid (PLA or PLLA), polyglyatic acid (PGA) polycaprolactone, polyanhydride, poly (ortho ester), and similar materials.

In the case of pre-malignant or malignant mucosa, the therapeutic agent may include a chemotherapeutic agent. A chemotherapeutic agent may then assist in the destruction of the mucosa. Alternatively, it is often advantageous to remove a portion of the mucosa for study. In this case, the chemotherapeutic agent may assist in destroying any residual pre-malignant or malignant tissue at the base of the mucosa or in the surrounding area. Preferably, the chemotherapeutic agent includes 5-fluorouracil, but any suitable chemotherapeutic agent may be used. Other types of therapeutic agents may also be used in addition to or in conjunction with chemotherapeutic agents, for example anti-inflammatories, coagulants, steroids, antibiotics, monoclonal antibodies, growth factors, cellular inhibitors, genetic therapeutics, or other suitable therapeutics.

Inner diffusion barrier 15 is disposed between elastomeric layer 11 and inner drug releasing layer 13. Inner diffusion barrier 15 prevents the therapeutic of inner drug releasing layer 13 from leeching into elastomeric layer 11 and into the body. Any suitable material may be used for inner diffusion barrier 15, but preferably the material is hydrophobic. Preferred materials include ethylene vinyl acetate, polyurethane, non-woven polyester sheeting, and other synthetic or natural elastomeric materials.

Figure 2:
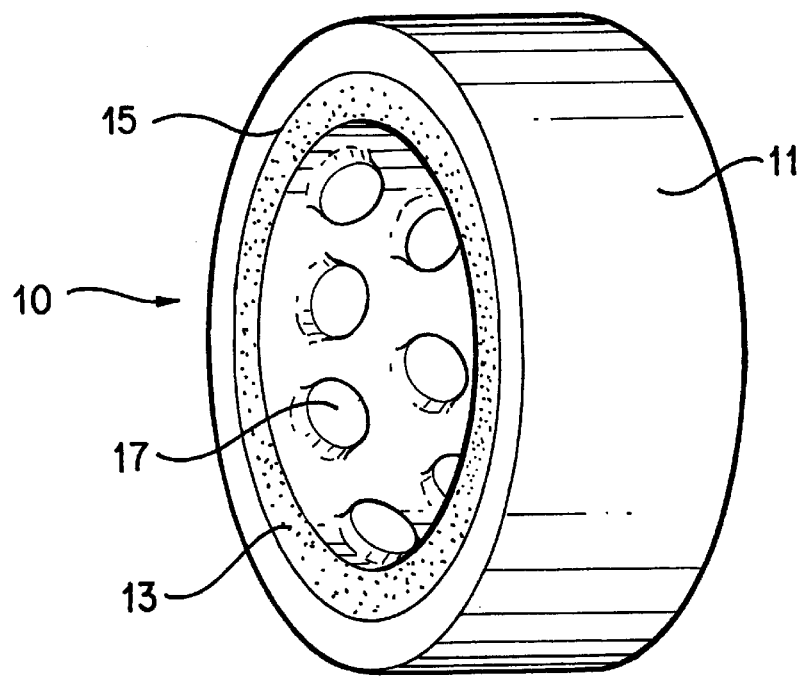
FIG. 2 is a perspective view of a second exemplary embodiment of a ligating band according to the present invention.

FIG. 2 illustrates an exemplary feature of a ligating band 10 according to the present invention. In some situations, for example when ligating mucosa in the digestive tract, ligating bands have a tendency to slip off the mucosa. This is sometimes due to natural tension created by ligation. In the digestive tract, this problem is exacerbated by peristolic contractions. For this reason, it is advantageous in some situations to provide protrusions 17 on inner drug releasing layer 13. Protrusions 17 extend into the mucosa and help maintain ligating band 10 in place. In addition, protrusions 17 assist in delivering the therapeutic agent to the target site. Preferably protrusions 17 include any therapeutic agent present on or within inner drug releasing layer 13, and may be constructed integral with inner drug releasing layer, if desired.

Figure 3:
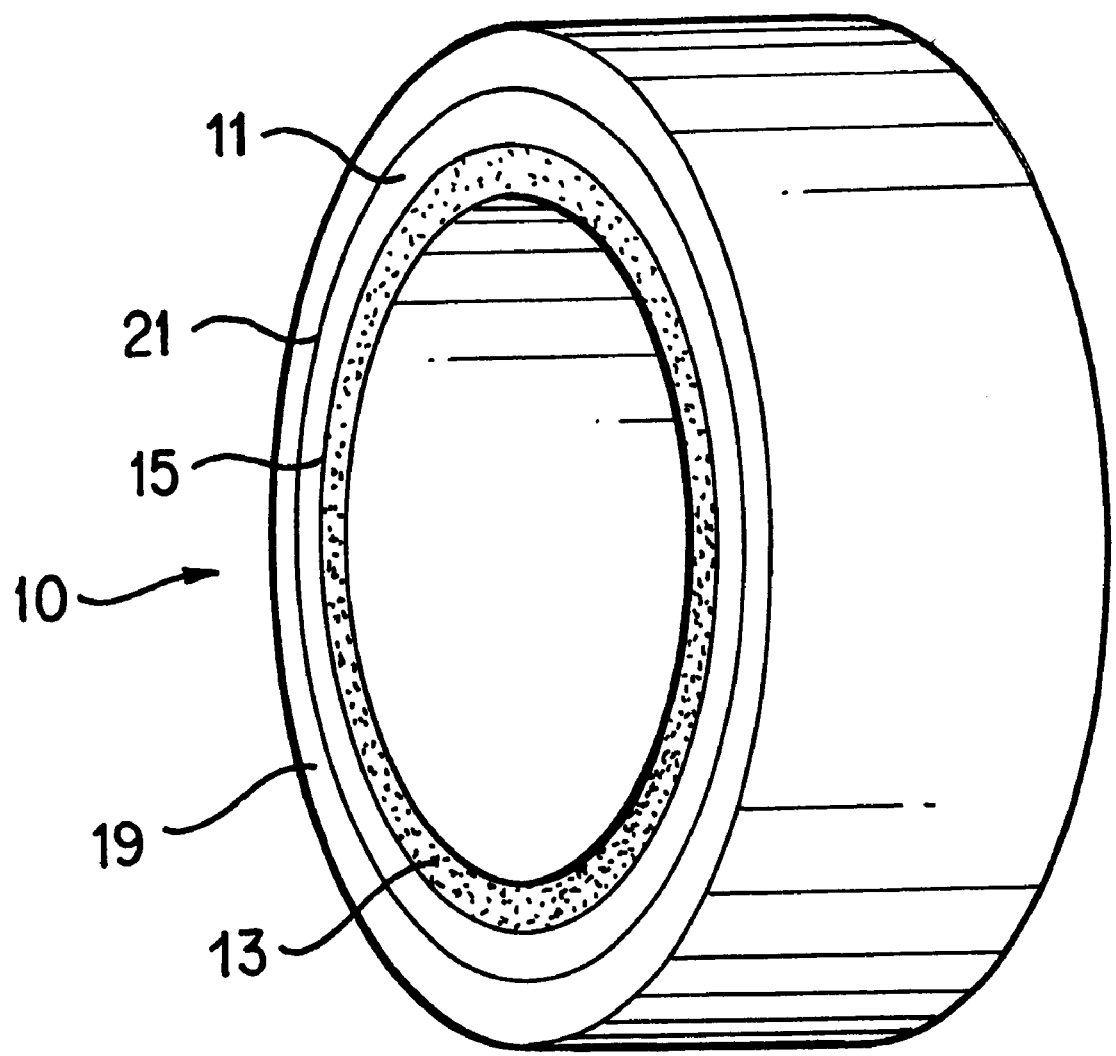
FIG. 3 is a perspective view of a third exemplary embodiment of a ligating band according to the present invention.
Figure 4:
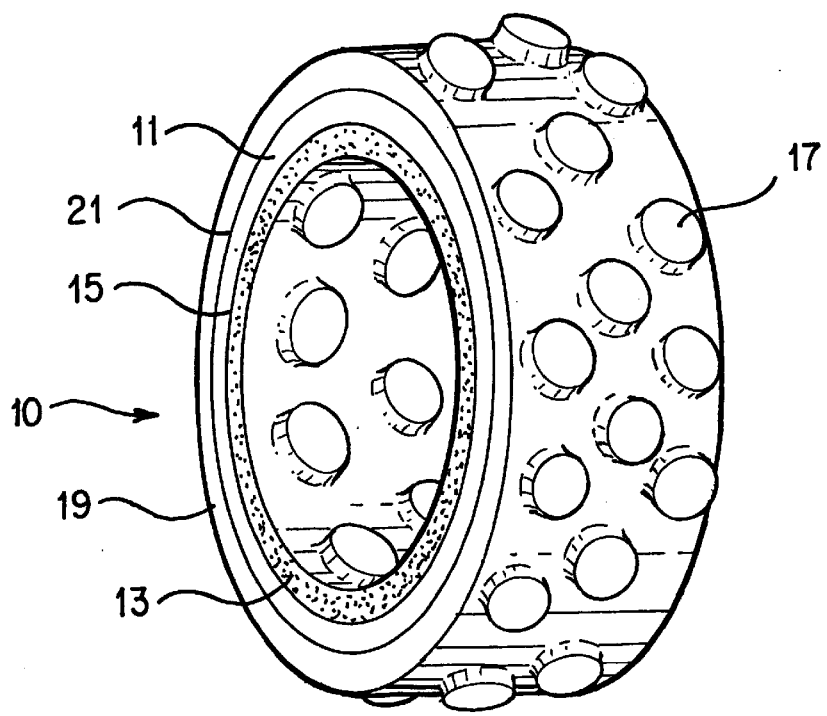
FIG. 4 is a perspective view of a fourth exemplary embodiment of a ligating band according to the present invention.

FIG. 3 shows another exemplary ligating band 10 according to the present invention. Some ligating band dispensers tend to roll the ligating band off a cylindrical end portion. Other ligating bands, even if not designed to have ligating bands roll during delivery, may allow the ligating band to become inverted during delivery. That is, the intended inner surface of the ligating band may end up facing outwardly. A ligating band 10 according to the present invention may therefore include an outer drug releasing layer 19, which may be separated from elastomeric layer 11 by an outer diffusion barrier 21. Outer drug releasing layer 19 and outer diffusion barrier 21 may be constructed from the same materials as inner drug releasing layer 13 and inner diffusion barrier 15, respectively, and outer drug releasing layer 19 preferably includes any therapeutics included on inner drug releasing layer 13. In this manner, if ligating band 10 is rotated inside-out during deployment, it may still administer the intended therapeutic or therapeutics to the target site. A ligating band 10 having outer drug releasing layer may also include protrusions 17 on either of inner and outer drug releasing layers, as illustrated in FIG. 4.

Figure 5:
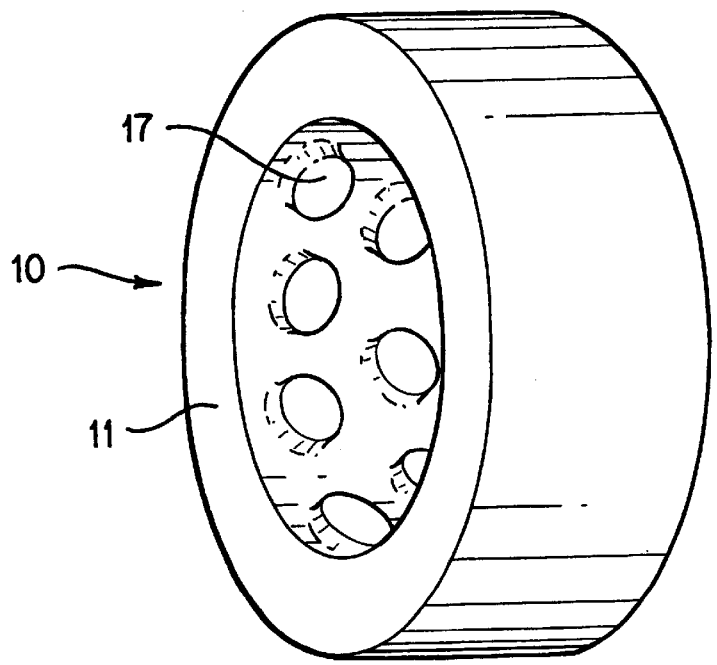
FIG. 5 is a perspective view of a fifth exemplary embodiment of a ligating band according to the present invention.

FIG. 5 illustrates an exemplary embodiment of a ligating band 10 according to the present invention, in which no inner drug releasing layer 13 or diffusion barrier 15, 21 are provided. In this embodiment, protrusions 17 are disposed directly on elastomeric layer 11. Protrusions 17 are embedded or coated with any desired therapeutic agents such as chemotherapeutic agents, and deliver the agents directly to the mucosa. Protrusions 17 are preferably formed of polycaprolactone, polyanhydride, poly (ortho ester), or a similar material, although any suitable material may be used.

Figure 6:
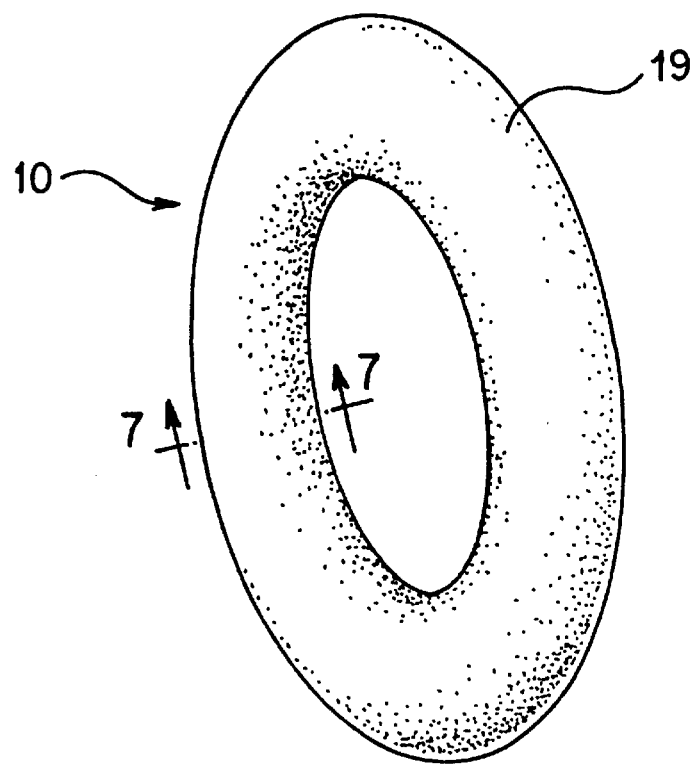
FIG. 6 is a perspective view of a sixth exemplary embodiment of a ligating band according to the present invention.
Figure 7:
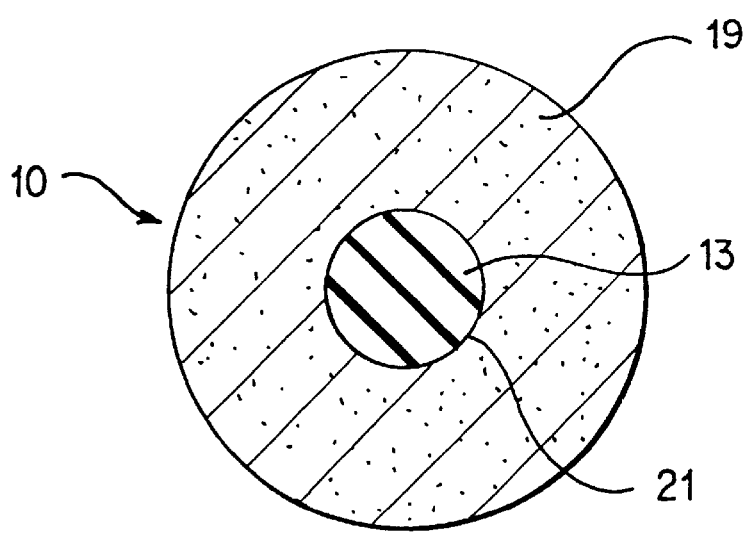
FIG. 7 is a cross-sectional view of the ligating band of FIG. 6, taken along the line 7—7 of FIG. 6.

FIGS. 6 and 7 illustrate an exemplary embodiment of a ligating band 10 according to the present invention also designed for delivery mechanisms that tend to roll the band. In this embodiment, ligating band 10 has a circular cross-section, as illustrated in FIG. 7. Specifically, elastomeric layer 13 is provided as an inner core, and is surrounded by outer drug releasing layer 19. As in other embodiments, the two layers 13, 19 are preferably separated by an outer diffusion barrier 21 (the term "outer" being used merely for convenience, as it was used for convenience in the description above). A ligating band 10 according to FIGS. 6 and 7 may also include protrusions 17 (not shown in FIGS. 6 and 7). The circular cross-section of a ligating band according to this embodiment ensures that outer drug releasing layer 19 will be in contact with the ligated mucosa, regardless of any rolling during deployment.

In an exemplary method of ligating tissue according to the present invention, a portion of tissue may first be removed, if desired, by any endoscopic procedure. This prior removal may be performed in order to retrieve tissue for biopsy, for example, or for any other suitable reason. Regardless of whether any "prior" tissue is removed, a ligating band dispenser may be introduced and delivered to the intended site. Tissue is then drawn into a recess of the ligating band dispenser, and a ligating band 10 including a chemotherapeutic or other therapeutic agent is delivered around the base of the tissue.

A ligating band and method according to the present invention has been described with respect to several exemplary embodiments. It can be understood, however, that there are many other variations of the above described embodiments which will be apparent to those skilled in the art. It is understood that these modifications are within the teaching of the present invention, which is to be limited only by the claims appended hereto.

What is claimed is:

1. A litigating band, comprising:
    a circular elastic band including:
    an elastomeric layer;
    an inner drug releasing layer, the inner drug releasing layer including a therapeutic agent; and
        an inner diffusion barrier disposed between the elastomeric layer and the inner drug releasing layer, each of the elastomeric layer and the inner drug releasing layer contacting the inner diffusion barrier.

2. The ligating band according to claim 1 wherein the therapeutic agent includes a chemotherapeutic agent.

3. The ligating. band according to claim 1, wherein the inner drug releasing layer is biodegradable.

4. The ligating band according to claim 1, further comprising at least one protrusion disposed on the inner releasing layer, the at least one protrusion including the therapeutic agent.

5. The ligating band according to claim 4, wherein the at least one protrusion is integral with the inner drug releasing layer.

6. The ligating band according to claim 4, wherein the therapeutic agent includes a chemotherapeutic agent.

7. The ligating band according to claim 1, further comprising:
    an outer drug releasing layer, the outer drug releasing layer including the therapeutic agent; and
    an outer diffusion barrier disposed between the elastomeric layer and the outer drug releasing layer, each of the elastomeric layer and the outer drug releasing layer contacting the outer diffusion barrier.

8. The ligating band according to claim 7 wherein the therapeutic agent includes a chemotherapeutic agent.

9. The ligating band according to claim 7, wherein the inner and outer drug releasing layers are biodegradable.

10. The ligating band according to claim 7, further comprising at least one inner protrusion disposed on the inner releasing layer and at least one outer protrusion disposed on the outer drug releasing layer, the at least one inner protrusion and the at least one outer protrusion including the therapeutic agent.

11. The ligating band according to claim 10, wherein the at least one protrusion is integral with the inner drug releasing layer and the at least one outer protrusion is integral with the outer drug releasing layer.

12. The ligating band according to claim 10, wherein the therapeutic agent includes a chemotherapeutic agent.

13. The ligating band according to claim 1, wherein the ligating band is circular in cross-section, the elastomeric layer being surrounded by the inner drug releasing layer.

14. The ligating band according to claim 13, wherein the therapeutic agent includes a chemotherapeutic agent.

15. The ligating band according to claim 13, wherein the inner drug releasing layer is biodegradable.

16. The ligating band according to claim 13, further comprising at least one protrusion disposed on the inner releasing layer, the at least one protrusion including the therapeutic agent.

17. The ligating band according to claim 16, wherein the at least one protrusion is integral with the inner drug releasing layer.

18. The ligating band according to claim 16, wherein the therapeutic agent includes a chemotherapeutic agent.

19. A ligating band, comprising:
a circular elastic band including:
an elastomeric layer; and
a drug releasing surface, the drug releasing surface including a chemotherapeutic agent.

20. The ligating band according to claim 19, wherein the drug releasing surface includes an inner drug releasing layer.

21. The ligating band according to claim 20, wherein the inner drug releasing layer is biodegradable.

22. The ligating band according to claim 19, wherein the drug releasing surface includes at least one protrusion.

23. The ligating band according to claim 22, wherein the at least one protrusion is biodegradable.

* * * * *

UNITED STATES PATENT AND TRADEMARK OFFICE
CERTIFICATE OF CORRECTION

PATENT NO.      : 6,471,987 B1
APPLICATION NO. : 09/328665
DATED           : October 29, 2002
INVENTOR(S)     : McBride-Sakal et al.

It is certified that error appears in the above-identified patent and that said Letters Patent is hereby corrected as shown below:

Column 2, line 51, "polyglyatic acid" should be changed to --polyglycolic acid--;

Column 3, line 6, "leeching" should be changed to --leaching--;

Column 3, line 18, "peristolic" should be changed to --peristaltic--; and

Column 3, line 27, "layer, if" should be changed to --layer 13, if--.

Claim 1, line 1 (column 4, line 36), "litigating" should be changed to --ligating--; and Claim 3, line 1 (column 4, line 47), "ligating. band" should be changed to --ligating band--.

Signed and Sealed this

Thirtieth Day of January, 2007

JON W. DUDAS
*Director of the United States Patent and Trademark Office*